(12) United States Patent
Ozasa et al.

(10) Patent No.: US 11,071,965 B2
(45) Date of Patent: Jul. 27, 2021

(54) FLOW REACTOR

(71) Applicant: KANEKA CORPORATION, Osaka (JP)

(72) Inventors: Shiori Ozasa, Takasago (JP); Takahiro Ohishi, Takasago (JP); Hiroaki Yasukouchi, Takasago (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 16/735,757

(22) Filed: Jan. 7, 2020

(65) Prior Publication Data

US 2020/0139339 A1 May 7, 2020

Related U.S. Application Data

(63) Continuation of application No. PCT/JP2018/022063, filed on Jun. 8, 2018.

(30) Foreign Application Priority Data

Jul. 31, 2017 (JP) ............................. JP2017-148083

(51) Int. Cl.
*B01J 19/24* (2006.01)
*C07C 263/10* (2006.01)
(Continued)

(52) U.S. Cl.
CPC ............. *B01J 19/24* (2013.01); *C07C 263/10* (2013.01); *B01J 8/0496* (2013.01);
(Continued)

(58) Field of Classification Search
USPC ................................................ 422/603, 644
See application file for complete search history.

(56) References Cited

U.S. PATENT DOCUMENTS

| 7,767,155 B2 * | 8/2010 | Ohta .................. B01L 3/565 |
|---|---|---|
| | | 422/503 |
| 9,446,375 B2 | 9/2016 | Kulkarni et al. |
| (Continued) | | |

FOREIGN PATENT DOCUMENTS

| JP | 2010-180184 A | 8/2010 |
|---|---|---|
| JP | 2012-140421 A | 7/2012 |
| (Continued) | | |

OTHER PUBLICATIONS

International Search Report dated Aug. 28, 2018 in PCT/JP2018/022063 filed on Jun. 8, 2018, 2 pages.
(Continued)

*Primary Examiner* — Fred M Teskin
(74) *Attorney, Agent, or Firm* — Oblon, McClelland, Maier & Neustadt, L.L.P.

(57) ABSTRACT

The purpose of the present invention is to provide a flow reactor that can ensure safety even if leakage occurs at the connections of the lines. The flow reactor of the present invention is characterized by including one or more line structures, each of the line structures including a raw material feeding line, a reactor unit to react a raw material fed from the raw material feeding line, and a discharge line to discharge a reaction product produced in the reactor unit, wherein the flow reactor includes a vessel in which part or all of the reactor unit and a fluid are accommodated to be capable of being in contact with each other, wherein each of the line structures includes two or more attachable and detachable connections, and wherein at least one of the attachable and detachable connections is accommodated in the vessel.

16 Claims, 5 Drawing Sheets

(51) Int. Cl.
*B01J 8/04* (2006.01)
*B01J 19/00* (2006.01)
(52) U.S. Cl.
CPC ........ *B01J 19/0013* (2013.01); *B01J 19/0093* (2013.01); *B01J 2219/00085* (2013.01); *B01J 2219/00166* (2013.01); *B01J 2219/24* (2013.01)

(56) References Cited

U.S. PATENT DOCUMENTS

| | | |
|---|---|---|
| 9,481,764 B1 | 11/2016 | Kinlen et al. |
| 2010/0112094 A1 | 5/2010 | Yoshida et al. |
| 2013/0217841 A1 | 8/2013 | Chiefari et al. |
| 2016/0046490 A1 | 2/2016 | Yoshida et al. |
| 2016/0090361 A1 | 3/2016 | Tweedie et al. |
| 2018/0118689 A1 | 5/2018 | Tweedie et al. |

FOREIGN PATENT DOCUMENTS

| | | |
|---|---|---|
| JP | 2013-543021 A | 11/2013 |
| JP | 2014-023982 A | 2/2014 |
| WO | WO 2008/047864 A1 | 4/2008 |
| WO | WO 2016/049509 A1 | 3/2016 |

OTHER PUBLICATIONS

Extended Search Report dated Feb. 15, 2021, in European patent application No. 18841200.1.

\* cited by examiner

FLOW REACTOR

CROSS-REFERENCE TO RELATED APPLICATIONS

This application is a continuation of International Application No. PCT/JP2018/022063, filed on Jun. 8, 2018, and claims priority to Japanese Application Number 2017-148083, filed on Jul. 31, 2017, the disclosures of which are incorporated herein by reference in their entireties.

TECHNICAL FIELD

The present invention relates to a flow reactor.

BACKGROUND ART

A micro-flow reactor is a chemical reaction apparatus generally utilizing a microchannel in the order of submillimeter as a reaction field. The micro-flow reactor has attracted attention in recent years because it has specific effects, due to the micro reaction field, such as high-speed mixing performance (for example, when two liquids are mixed in a micro-space, the substance diffusion distance in the two liquids decreases, resulting in shortening the time of mass transfer movement), heat removal efficiency (since the reaction field is small, thermal efficiency is extremely high and temperature control is easy), reaction control performance, interface control performance, or the like. In addition, it is expected that the technology of the micro-flow reactor provides various effects such as improved safety and significantly reduced cost of equipment along with downsizing of the whole process, process intensification (micro in macro) by incorporating into existing processes, and production of substances that could not be produced by an existing production method.

The micro-flow reactor has a problem that only a limited amount can be processed at a time. Therefore, process development of a flow reactor which can be practically used even if a processing amount increases is being carried out. The flow reactor is a chemical reaction apparatus in which the diameter of a flow channel is enlarged to the order of millimeters to centimeters to the extent that the characteristics of the micro-flow reactor are not impaired to enhance the operability. The flow reactor is mainly composed of a raw material feeding line, a reaction unit, and an operation control unit (such as, for example, Patent Document 1).

RELATED ART DOCUMENTS

Patent Document

Patent Document 1: JP 2013-543021 (A)

SUMMARY OF THE INVENTION

Problems to be Solved by the Invention

However, the flow reactor is configured with a plurality of lines connected to each other, and there is a concern that leakage may occur at the connections of the lines. If leakage occurs, the leakage continues until a liquid-feeding stop signal is transmitted to an operation controller, resulting in polluting the surrounding environment. In particular, if a leaked substance is a dangerous substance, the damage to the surroundings increases.

The present invention has been made by focusing on the above situation, and an object of the present invention is to provide a flow reactor that can ensure safety even if leakage occurs at the connections of the lines.

Solutions to the Problems

As a result of intensive studies for achieving the above object, the inventors have found that when a connection of the lines is accommodated in a vessel in which a reactor unit and a fluid are accommodated to be capable of being in contact with each other, even if leakage occurs at the connection of the lines, the leaked substance remains in the vessel and can be appropriately handled by using the fluid in the vessel, so that safety can be ensured, and completed the present invention accordingly.

That is, the present invention is as follows:

[1] A flow reactor comprising one or more line structures, each of the line structures comprising a raw material feeding line, a reactor unit to react a raw material fed from the raw material feeding line, and a discharge line to discharge a reaction product produced in the reactor unit, wherein the flow reactor comprises a vessel in which part or all of the reactor unit and a fluid are accommodated to be capable of being in contact with each other, wherein each of the line structures comprises two or more attachable and detachable connections, and wherein at least one of the attachable and detachable connections is accommodated in the vessel.

[2] The flow reactor according to [1], wherein at least one of the line structures comprises two or more raw material feeding lines, and further comprises, between the raw material feeding lines and the reactor unit, a mixing unit to mix raw materials fed from the two or more raw material feeding lines and send a mixture to the reactor unit.

[3] The flow reactor according to [1] or [2], wherein the attachable and detachable connections are arranged on an upstream side of the reactor unit and a downstream side of the reactor unit in each of the line structures.

[4] The flow reactor according to [2], wherein the attachable and detachable connections are arranged on an upstream side of the mixing unit and a downstream side of the reactor unit in each of the line structures.

[5] The flow reactor according to any of [1] to [4], wherein two or more of the attachable and detachable connections are accommodated in the vessel.

[6] The flow reactor according to any of [1] to [5], wherein the fluid is a liquid and is capable either of quenching a leaked substance from the line structures, of having a characteristic changeable when contacting the leaked substance, of being heat-exchanged with at least part of the line structures, or of supporting the reactor unit.

[7] The flow reactor according to [6], wherein the vessel accommodate a liquid as the fluid, the space where there isn't the liquid is filled with a gas, and one or more part of the reactor unit is exposed to the gas portion without contacting the liquid.

[8] The flow reactor according to any of [1] to [7], wherein the vessel is a closed vessel capable of isolating contents of the vessel from outside.

[9] The flow reactor according to any of [1] to [8], wherein the reactor unit has a flow channel with an inner diameter of 0.1 mm or more and 50 mm or less.

[10] The flow reactor according to any of [1] to [9], wherein the reactor unit has a shape with at least one bent part.

[11] A manufacturing facility comprising the flow reactor according to any of [1] to [10].

[12] The manufacturing facility according to [11], wherein the fluid accommodated in the vessel of the flow reactor is a medium whose characteristic is changeable when contacting a reaction liquid, and the manufacturing facility comprises a sensor capable of detecting the change of the characteristic.

[13] A method for using the manufacturing facility according to [11] or [12], the method comprising: when a raw material is fed to the manufacturing facility to obtain a reaction product, selecting two or more of the attachable and detachable connections to remove a section between the two or more connections, and replacing with a new configuration comprising one or more selected from line structure components including a raw material feeding line, a mixing unit, a reactor unit, and a discharge line.

[14] The method according to [13] comprising:

stopping a flow stream from the raw material to the reaction product, and after replacing the section between the connections and changing the raw material, starting the flow stream.

[15] The method according to [13] comprising:

stopping a flow stream from the raw material to the reaction product, and after replacing the section between the connections and performing one or more selected from an outage, routine check, and one or more parts replacement of the manufacturing facility, starting the flow stream.

Effects of the Invention

According to the present invention, the connection of the lines is accommodated in the vessel in which the reactor unit and the fluid are accommodated to be capable of being in contact with each other, and even if leakage occurs at this connection of the lines, a leaked substance remains in the vessel, so that safety can be ensured.

MODE FOR CARRYING OUT THE INVENTION

As for the entire line set of a flow reactor, there are an infinite number of variations depending on a reaction mode to be performed. Hereinafter, the present invention will be illustrated and described with reference to representative examples. However, the present invention is not intended to be limited to examples illustrated and described below and can also be carried out with appropriate modifications within the scope of the invention, and such modifications are included in the technical scope of the invention.

(1) First Example

[First step: Compound A+Compound B→Compound C];
[Second step: Compound D→Compound E]; and
[Third step: Compound C+Compound E→Compound F]

Figure 1:
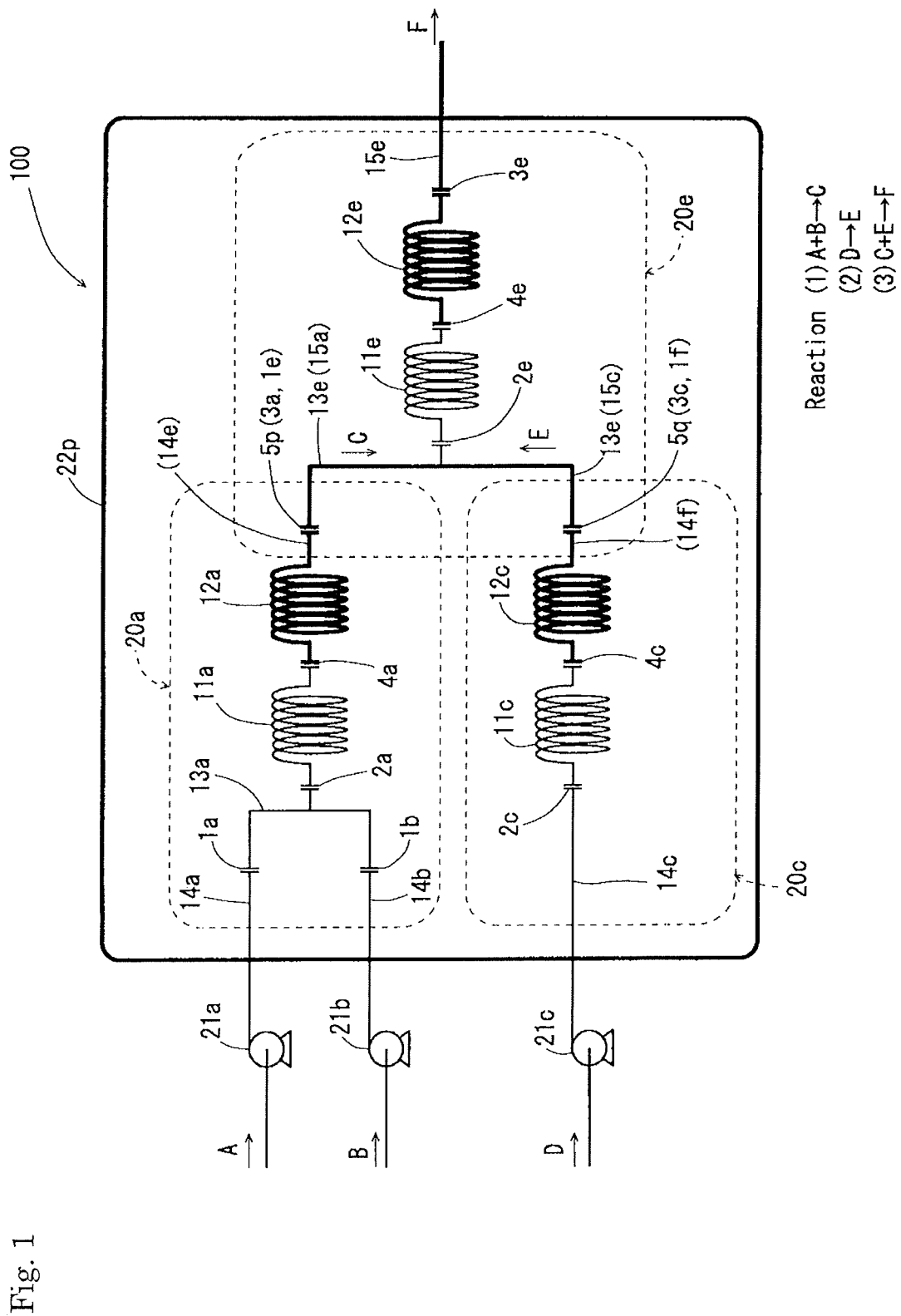
FIG. 1 is a schematic view showing one example of a flow reactor of the present invention.

FIG. 1 is a schematic view showing a first example of the flow reactor of the present invention, the first example having a line set assuming the above three-step reaction.

Specifically, a flow reactor 100 of FIG. 1 includes a line structure 20a for performing the first step, a line structure 20c for performing the second step, and a line structure 20e for performing the third step. The line structure 20c for the second step is characterized by feeding only one kind of raw material (D) (hereinafter, a line structure for feeding one kind of raw material may be referred to as an A-type line structure). The line structure 20a for the first step and the line structure 20e for the third step are common in that two kinds of raw materials are mixed to be allowed to react (hereinafter, a line structure for feeding a plurality of raw materials may be referred to as a B-type line structure). These line structures have each an appropriate configuration based on such a characteristic or commonality. Specifically, the line structure 20c, which falls under the A-type line structure, includes a single raw material feeding line 14c, reactor units 11c and 12c to react a raw material (D) fed from the raw material feeding line 14c, and a discharge line 15c to discharge a reaction product produced in the reactor units 11c and 12c. On the other hand, each of the line structures 20a and 20e, which fall under the B-type line structure, includes two raw material feeding lines (14a and 14b, or 14e and 14f), reactor units (11a and 12a, or 11e and 12e) to react raw materials (A and B, or C and E) fed from the raw material feeding lines (14a and 14b, or 14e and 140, a discharge line (15a or 15e) to discharge a reaction product produced in the reactor units (11a and 12a, or 11e and 12e), and further includes, between the raw material feeding lines (14a and 14b, or 14e and 140 and the reactor unit (11a or 11e), a mixing unit (13a or 13e) to mix the raw materials (A and B, or C and E) fed from the raw material feeding lines (14a and 14b, or 14e and 140 and send the mixture to the reactor unit.

As in the example of FIG. 1, when the line structures 20a, 20c, and 20e are provided and have a relationship in which one line structure 20e uses the reaction products (discharged materials) of the other line structures 20a and 20c as raw materials, the line structures on the upstream side may also serve as raw material feeding lines for the line structure on the downstream side, and the line structure on the downstream side may also serve as a discharge line for the line structures on the upstream side. In the example of FIG. 1, part of the line structure 20a on the upstream side (specifically, the downstream part of the reactor unit 12a) also serves as the raw material feeding line 14e of the line structure 20e on the downstream side, and part of the line structure 20e on the downstream side (specifically, the upstream part of the raw material mixing unit 13e) also serves as the discharge line 15a of the line structure 20a on the upstream side. The same relationship applied to the relationship between the line structure 20c and the line structure 20e.

Each of the line structures has two or more attachable and detachable connections (hereinafter sometimes referred to as attachable and detachable parts). When a plurality of line structures are included as in the illustrated example, two or more attachable and detachable parts are provided in the entire line structures. Specifically, among joint portions 1a, 1b, 1e and 1f of the raw material feeding lines 14a, 14b, 14e and 14f and the mixing units 13a and 13e; joint portions 2a, 2c and 2e of the mixing units 13a, 13e or the raw material feeding line 14c and the reactor units 11a, 11c and 11e; joint portions 3a, 3c and 3e of the reactor units 12a, 12c and 12e and the discharge lines 15a, 15c and 15e; joint portions 4a, 4c and 4e between the parts 11a, 12a, 11c, 12c, 11e and 12e of the reactor unit; and joint portions 5p and 5q between the line structures, two or more joint portions are configured as attachable and detachable parts. By including two or more attachable and detachable parts, a section between the two attachable and detachable parts can be removed and replaced with the same or another configuration depending on the selection of two attachable and detachable parts. The two or more attachable and detachable parts are preferably selected so as to be a combination in which that a section between the attachable and detachable parts can be removed or replaced. As long as the section between the two attachable and detachable parts can be removed or replaced, the number of the attachable and detachable parts is not limited to two and may be three or more, or all of the joint portions may be attachable and detachable parts. When the joint portion is not an attachable and detachable part, the joint portion may be a portion of continuous piping or a welded portion.

In the present invention, at least one (all in the illustrated example) of the attachable and detachable parts is accommodated in a vessel 22p. Therefore, even if leakage occurs at this connection, a leaked substance remains in the vessel 22p, and safety can be ensured.

Furthermore, in the present invention, a fluid is accommodated in the vessel 22p, and part or all (all in the illustrated example) of the reactor units 11a, 12a, 11c, 12c, 11e and 12e are accommodated in the vessel 22p. When the fluid is accommodated in the vessel, and the reactor units are accommodated to be capable of being in contact with the fluid, it is possible to give various functions to the fluid and improve the usefulness of the flow reactor 100.

(2) Second Example

[First Step: Compound K+Compound L→Compound M]

The basic concept of the flow reactor shown in the first example is the same even if the assumption reaction, that is, the entire line set changes. A flow reactor 101 in FIG. 2 has a line set assuming the above first step reaction, and thus includes a single B-type line structure 20g for two kinds of raw materials. Specifically, the flow reactor 101 includes a single line structure composed of two raw material feeding lines 14g and 14h, a reactor unit 11g to react raw materials (K and L) fed from the raw material feeding lines 14g and 14h, a discharge line 15g to discharge a reaction product produced in the reactor unit 11g, and a mixing unit 13g to mix the raw materials (K and L) fed from the raw material feeding line 14g and 14h and send the mixture to the reactor unit 11g.

Figure 2:
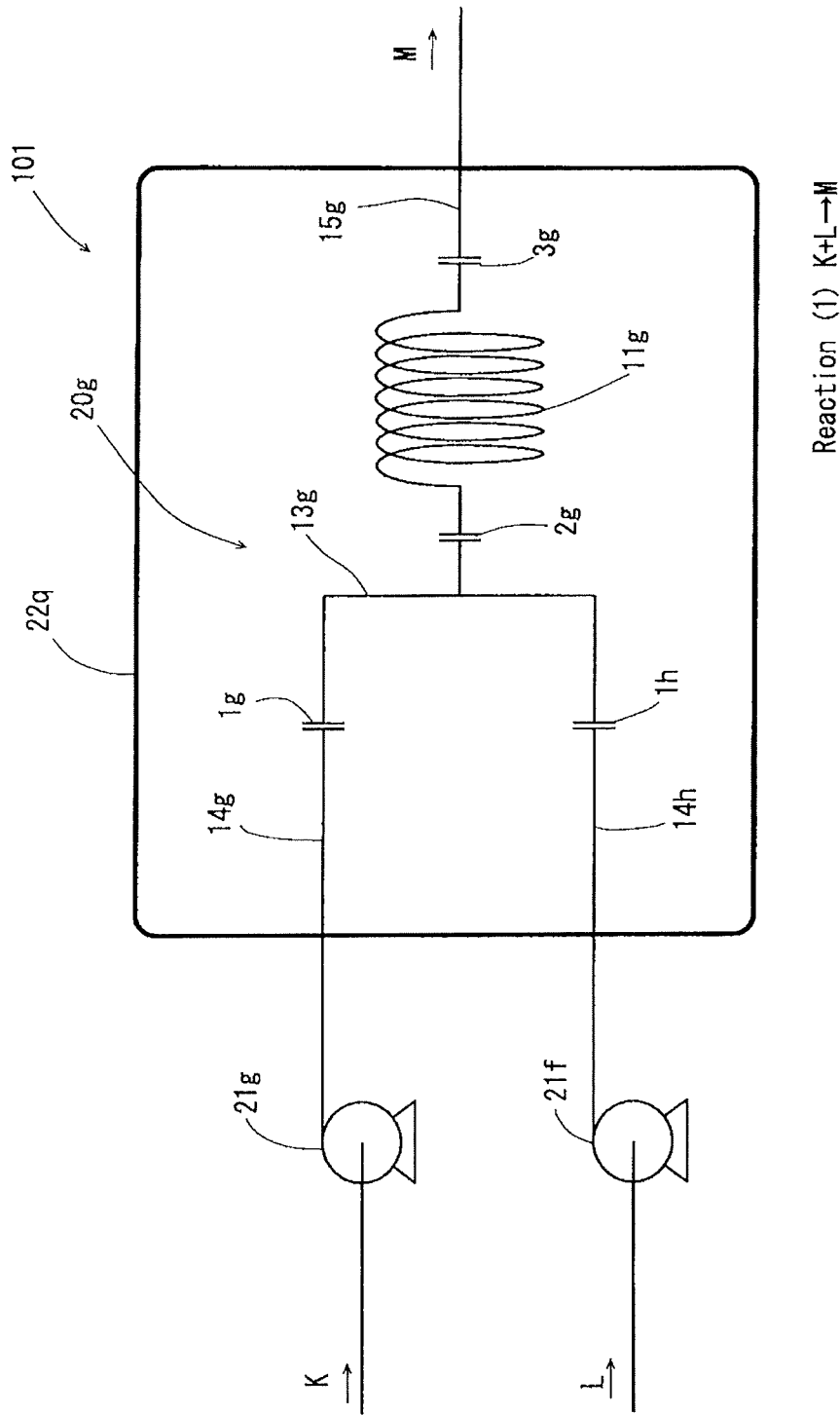
FIG. 2 is a schematic view showing another example of a flow reactor of the present invention.

In the example of FIG. 2 as well, the line structure has two or more attachable and detachable parts as a whole. Specifically, among joint portions 1g and 1h of the raw material feeding lines 14g and 14h and the mixing unit 13g; a joint portion 2g of the mixing unit 13g and the reactor unit 11g; and a joint portion 3g of the reactor unit 11g and the discharge line 15g, two or more joint portions are configured as attachable and detachable parts. When the reactor unit 11g is divided into two or more parts, it is sufficient that two or more joint portions among all the joint portions including joint portions between the parts of the reactor unit are configured as attachable and detachable parts.

In addition, in the example of FIG. 2 as well, at least one (all in the illustrated example) of the attachable and detachable parts is accommodated in a vessel 22q. Furthermore, in the example of FIG. 2 as well, a fluid is accommodated in the vessel 22q, and part or all (all in the illustrated example) of the reactor unit 11g is accommodated in the vessel 22q.

In the flow reactor of the present invention including the examples of FIG. 1 and FIG. 2, it is recommended to appropriately select (set) a combination of attachable and detachable parts from the above-described joint portions so that a section between the attachable and detachable parts can be removed and replaced with another configuration. For example, in the selection (setting) of a combination of the attachable and detachable parts, the combination may be selected (set) such that each line structure can be individually removed, such that part of a line structure can be removed, or such that a section across a plurality of line structures can be removed. Removal of each line structure is explained with reference to the illustrated example. For example, when the joint portions 1a and 1b between the mixing unit 13a and the raw material feeding lines 14a and 14b, and the joint portion 3a between the reactor unit 12a and the discharge line 15a are configured as attachable and detachable parts, the line structure 20a can be individually removed. The same applies to the other B-type line structures 20e and 20g for two kinds of raw materials. In the A-type line structure 20c having a single raw material feeding line, if the joint portion 2c between the raw material feeding line 14c and the reactor unit 11c and the joint portion 3c between the reactor unit 12c and the discharge line 15c are configured as attachable and detachable parts, the line structure 20c can be individually removed.

An example in which part of a line structure can be removed is explained with reference to the illustrated example. When two or more joint portions are appropriately selected, as attachable and detachable parts, from among 2a, 2c, 2e and 2g located immediately before the reactor unit (when the reactor units are continuously arranged, portions corresponding between the parts of the reactor units are not included), 4a, 4c and 4e between the parts of the reactor units, and 3a, 3c, 3e and 3g located immediately after the reactor unit (when the reactor units are continuously arranged, portions corresponding between the parts of the reactor units are not included), any parts of the reactor units such as the first halves 11a, 11c and 11e of the reactor units, the second halves 12a, 12c and 12e of the reactor units, or all of the reactor units (11a+12a, 11c+12c, 11e+12e, 11g) can be removed.

There are many examples in which a section across line structures can be removed. One example thereof is such that one joint portion (for example, 4a) in the first line structure 20a, one joint portion (for example, 4c) in the second line structure 20c, and one joint portion (for example, 2e) in the third line structure 20e are configured as attachable and detachable parts.

As one example of a preferable combination of the attachable and detachable parts, in the case of assuming removal of a specific reactor unit (for example, 11a), a combination of a joint portion (for example, a set of the joint portions 1a and 1b, or the joint portion 2a) on the upstream side of the reactor unit and a joint portion (for example, the joint portion 4a or 5p (which is also 3a or 1e)) on the downstream of the reactor unit can be mentioned. Such a combination makes it possible to remove the reactor unit (11a in this example) to be removed. The similar combination in the example of FIG. 2 is a combination of a set of the joint portions 1g and 1h or the joint portion 2g, and the joint portion 3g.

As another example of a preferable combination of the attachable and detachable parts, in the case of assuming removal of a specific reactor unit (for example, 11a) together with a mixing unit (for example, 13a), a combination of a joint portion (for example, a set of the joint portions 1a and 1b) on the upstream side of the mixing unit and a joint portion (for example, the joint portion 4a or 5p (which is also 3a or 1e)) on the downstream of the reactor unit can be mentioned. Such a combination makes it possible to remove the reactor unit to be removed together with the mixing unit. The similar combination in the example of FIG. 2 is a combination of a set of the joint portions 1g and 1h and the joint portion 3g.

Although it is sufficient that at least one of the attachable and detachable parts is accommodated in the vessel 22p, 22q, it is preferred that two or more of the attachable and detachable parts are accommodated in the vessel 22p, 22q. More preferably, the attachable and detachable parts required for removal or replacement are all accommodated in the vessel 22p, 22q. As for the attachable and detachable parts accommodated in the vessel, some of the attachable and detachable parts may be in contact with the fluid in the vessel, or all of the attachable and detachable parts may be in contact with the fluid in the vessel. It is preferred that all of the attachable and detachable parts can be in contact with the fluid. For example, when the fluid is a liquid, some of the attachable and detachable parts in the vessel may be immersed in the liquid, or all of the attachable and detachable parts may be immersed in the liquid. It is preferred that all of the attachable and detachable parts are immersed in the liquid.

A form of the attachable and detachable part may be suitably selected, and examples thereof include a flange structure, a screw connection structure, and a coupler connection structure.

A means for passing a raw material through each of the raw material feeding lines 14a, 14b, 14c, 14g, and 14h of the flow reactors as described above can be appropriately selected according to the state (liquid, gas, or dispersion) of the raw material, the stability of the raw material, and the like. When the raw material is a liquid (including a solution), it is recommended to use pumps 21a, 21b, 21c, 21g, and 21f.

In the A-type line structure 20c having a single raw material feeding line, the reaction may be initiated based on a temperature (for example, by using a fluid to heat the reactor units 11c and 12c to a reaction initiation point or higher) or by using a reaction accelerator such as a catalyst or an initiator. The reaction accelerator can be placed in an appropriate position (inside the reactor) including the inner walls of the reactor units 11c and 12c.

In the B-type line structures 20a, 20e and 20g each having a plurality of raw material feeding lines and using a mixing unit, the number of the raw material feeding lines can be appropriately increased or decreased according to the kind of raw material and according to the mixing procedure. For example, when three raw materials are fed separately, three raw material feeding lines corresponding to the respective raw materials are used, and the three raw materials may be mixed at the same time in one mixing unit, or two of the three raw materials may be mixed in one mixing unit and then the resulting mixture may be mixed with the remaining raw material in another mixing unit. Even in the case of using two kinds of raw materials A and B, the raw material A is divided into two portions (raw material A1 and raw material A2), the raw material A1 and the raw material B are mixed, and then the raw material A2 may be mixed with this mixture. In such a case, the number of raw material feeding lines is larger than the number of kinds of raw materials.

The reactor unit may be the reactor unit 11g composed of a single part, and may be the reactor unit (11a and 12a, 11c and 12c, 11e and 12e) divided into two or more parts (two parts in the illustrated example) in the flow direction of the reaction fluid. In the case of the reactor unit divided into two or more parts, the shape of the reactor unit 11a, 11c, or 11e on the upstream side may or may not be equal to the shape of the reactor unit 12a, 12c, or 12e on the downstream side. For example, the inner diameter of the reactor unit on the upstream side may be smaller or larger than the inner diameter of the reactor unit on the downstream side. The length of the reactor unit on the upstream side may be shorter or longer than the length of the reactor unit on the downstream side. The shape, inner diameter, and length of the reactor unit as described above can be appropriately selected according to the reaction type and the required retention time. The design of the inner diameter of the reactor unit is not limited to the above example. For example, the mixing efficiency improves as the inner diameter of the reactor unit decreases, and the pressure drop can reduce as the inner diameter of the reactor unit increases. Therefore, the reaction can be allowed to proceed efficiently by decreasing the inner diameter of the reactor unit on the upstream side and increasing the inner diameter of the reactor unit on the downstream side.

In the case of the reactor unit divided into two or more parts, a joint portion between the parts may be an attachable and detachable part that can be removed or replaced depending on a mode of use, or may be a portion of continuous piping or a welded portion. For example, by forming the joint portion as an attachable and detachable part that can be removed or replaced, it is possible to replace only an appropriate section with a new configuration. Moreover, by using continuous piping or joint by welding, it is possible to reduce the risk of leakage from the joint portions, resulting in safe use.

As described above, all of the reactor unit may be capable of being in contact with the fluid in the vessel 22p, 22q, but only part of the reactor unit may be capable of being in contact with the fluid. For example, when the fluid is a liquid, only part of the reactor unit may be immersed in the liquid, and the remaining part may be exposed to gas. In the case where only part of the reactor unit is immersed in the liquid, when the reactor unit is divided into two or more parts, each of the two or more parts of the reactor unit may be individually immersed.

The line shape of each of the reactor units 11a, 12a, 11c, 12c, 11e, 12e, and 11g is not particularly limited, and may be linear, columnar, spiral, or coiled. The line shape is preferably a shape with at least one bent part. This shape with at least one bent part includes a shape with at least one bent back. By configuring the reactor unit in a non-linear shape, like a reactor unit wound in the shape of a spiral or coil, or a reactor unit with several bent backs, minimizing of the flow reactor can be achieved. The reactor unit is preferably in a shape with an unvaried curvature like the shape of a straight line, spiral, coil, or the like. Non-uniformity in flow can be prevented by making the reactor unit in the shape having an unvaried curvature. The axial direction of the spiral or coil is not particularly limited, and may be parallel to the direction of gravity or perpendicular to the direction of gravity, but is more preferably parallel to the direction of gravity. By adjusting the shape of the reactor unit as mentioned above, the operation of attaching and detaching can be smoothly performed without the connections and the flow channel obstructing each other.

A material for the reactor unit can be selected from various materials, and may be appropriately selected depending on needs for solvent resistance, pressure resistance, heat resistance, or the like. For example, the reactor unit may be made of stainless steel such as SUS304, SUS316, and SUS316L, a corrosion-resistant metal such as Hastelloy and Inconel, a nonferrous metal such as titanium, copper, nickel, and aluminum, ceramics, which may be glass, (such as an inorganic sintered material), SiC, and a resin such as PEEK resin, silicone resin, and fluororesin.

The inner diameter of the reactor unit is, for example, 0.1 mm or more, preferably 0.2 mm or more, and more preferably 0.3 mm or more, and is, for example, 50 mm or less, preferably 10 mm or less, and more preferably 5 mm or less.

The length (entire length) of the reactor unit is preferably 1 cm or more, and more preferably 10 cm or more. The upper limit of the length of the reactor unit is not particularly limited, and is preferably 500 m or less, and more preferably 300 m or less. The length of the reactor unit may be appropriately determined according to a retention time and the like.

The mixing unit may be equipped with a known mixer in order to sufficiently stir the raw materials. Examples of such a mixer include a T-shape mixer, a Y-shape mixer, a static mixer, a helix-type mixer, and the like.

The number of line structures (A-type line structure, B-type line structure, and the like) constituting the flow reactor may be any of one, two, three, or four or more, and is preferably three or less.

In the flow reactor of the present invention, it is desirable to properly select a fluid accommodated in the vessel $22p$, $22q$ to cause the fluid to provide various functions. For example, using an inert gas or a non-reactive solution as the fluid is helpful to prevent ignition, even if a highly flammable substance leaks from the connections. When a fluid whose characteristics (for example, color, light scattering, pH, etc.) change due to contact with a leaked substance is used, it is possible to detect leakage from the connections and take appropriate measures against the leakage (for example, stop of feeding of raw materials) by observing such change in physical characteristics. Furthermore, when a fluid (such as a quench liquid for a raw material, reaction liquid, solvent, etc.) that reacts with a leaked substance (a raw material, reaction liquid, solvent, etc.) from the line structures $20a$, $20c$, $20e$, and $20g$ to be capable of making the leaked substances harmless is used, even if leakage occurs from the connections, higher safety can be maintained. In addition, using a heating medium or a cooling medium as the fluid is helpful to perform heating or heat removal at least part of the line structure by heat exchange. As the line structure to be subjected to heating or heat removal, a raw material feeding line, a mixing unit, a reactor unit, a discharge line, and the like can be mentioned. In particular, it is assumed that part of the reactor unit is subjected to heating or heat removal. When a heating medium or a cooling medium is used as the fluid to perform heating or heat removal of at least part of the reactor unit, the lower limit of the volume percentage of the part of the reactor unit to the entire reactor unit is not particularly limited, and, for example, is preferably 20% or more, more preferably 30% or more, and further preferably 40% or more. The upper limit of the volume percentage of the part of the reactor unit to the entire reactor unit is not particularly limited, and, for example, is preferably 90% or less, more preferably 80% or less, and further preferably 70% or less. When the reactor unit is made of a material with a relatively low specific gravity, such as a resin, the use of a liquid as the fluid allows the reactor unit to be supported and be also prevented from being sagged by its weight. The fluid is preferably a liquid, more preferably water, an aqueous solution, alcohol, or ether, and further preferably water or an aqueous solution.

When the fluid is a liquid, the lower limit of the amount (capacity) of the liquid with respect to the size (hereinafter referred to as a fluid accommodation size) of the vessel excluding the line structures inside the vessel is not particularly limited. For example, the volume ratio of the liquid with respect to 100 volume of the fluid accommodation size is preferably 5 or more, more preferably 50 or more, and further preferably 80 or more. The presence of the fluid in a sufficient amount with respect to the amount of a liquid leaking from the line structures into the vessel makes it possible to improve the accuracy or efficiency for rendering a leaked substance harmless by the fluid or for heating or cooling the reactor by the fluid.

The vessel $22p$ and the vessel $22q$ may have an opening on a portion (for example, on the upper portion) of the vessel, and is preferably a closed vessel, such as a vessel with no opening or with an opening being closed, that is capable of isolating the contents from the outside. Such a closed vessel may have an outlet and an inlet, such as piping for taking in and out the fluid accommodated in the vessel.

The size (internal capacity, etc.) of the vessel $22p$ or the vessel $22q$ is not particularly limited, and is preferably 0.05 L or more, more preferably 0.1 L or more, further preferably 0.5 L or more, and still further preferably 5 L or more. The upper limit of the size (internal capacity, etc.) is not particularly limited, and is preferably 1000 L or less, and more preferably 500 L or less. By thus adjusting the size of the vessel, it becomes easy to install a device to detect a change in the characteristics of the fluid in the vessel in the event of leakage. In addition, when the size of the vessel is 1000 L or less, the fluid in the vessel is easily diffused, so that the uniformity of fluid characteristics can be improved, and it is possible to improve the accuracy or efficiency for detecting leakage through the fluid, for rendering a leaked substance harmless by the fluid, or for heating or cooling the reactor by the fluid. Therefore, for example, when leakage from the connections occurs, it is possible to take appropriate measures against the leakage by quickly and accurately detecting a change in the characteristics of the fluid, and higher safety can be maintained.

The lower limit of the size (internal capacity) of the vessel $22p$ or the vessel $22q$ with respect to the total size (internal capacity) of all the line structures of the flow reactor is not particularly limited. The volume ratio of the internal volume of the vessel to the total internal volume of all the line structures is preferably 2 times or more, more preferably 5 times or more, and further preferably 10 times or more. By thus adjusting the internal volume of the vessel to be larger than the total internal volume of all the line structures, when the liquid in the line structures leaks into the vessel, it is possible to keep the leaked liquid inside the vessel and effectively suppress leakage to the outside of the vessel. The presence of the fluid in a sufficient amount with respect to the amount of a liquid leaking from the line structures into the vessel makes it possible to improve the accuracy or efficiency for rendering a leaked substance harmless by the fluid or for heating or cooling the reactor by the fluid.

The upper limit of the internal volume (volume ratio) of the vessel with respect to the total internal volume of all the line structures is also not particularly limited, and is preferably 5000 times or less, more preferably 2500 times or less, and further preferably 1000 times or less. When the liquid in the line structures leaks into the vessel whose volume ratio is 5000 times or less, it is possible to detect leakage from the connections by observing a change in the characteristics (color, light scattering, pH, etc.) of the fluid in the vessel with a conventional detector and appropriate measures against the leakage can be taken.

(3) Manufacturing Facility

Figure 3:
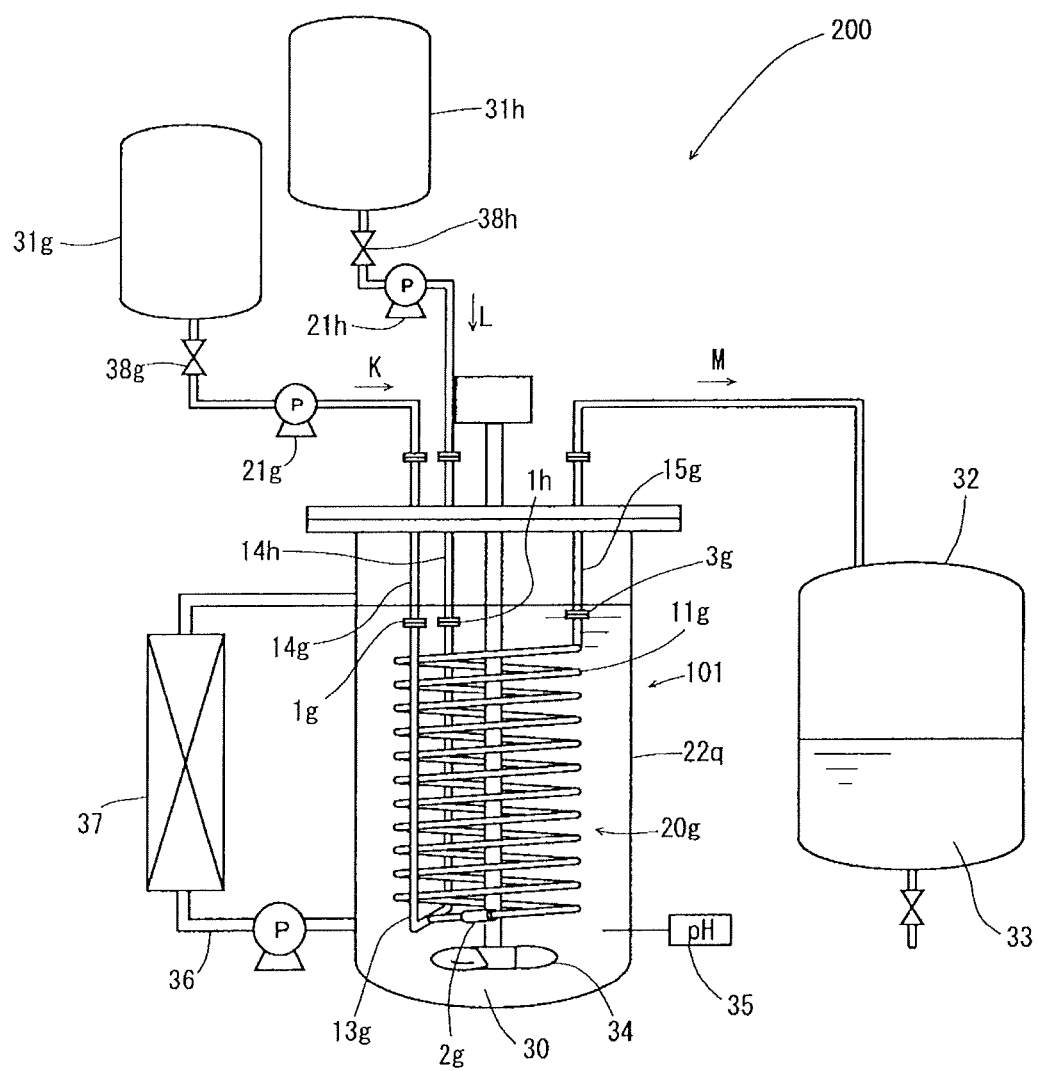
FIG. 3 is a schematic view showing one example of a manufacturing facility using a flow reactor of the present invention.

FIG. 3 shows one example of a manufacturing facility equipped with the above flow reactor. More specifically, the manufacturing facility includes a flow reactor in which the example of FIG. 2 is more limited in that a closed vessel is adopted as the vessel 22$q$, in that a liquid (water in the illustrated example) is accommodated in the vessel as the fluid, and in that the entire reactor part 11$g$ and the attachable and detachable parts 1$g$, 1$h$, 3$g$ and 2$g$ in the vessel are immersed in this liquid. The explanation of this manufacturing facility is applicable to the scope including the flow reactor of FIG. 2 and even to the scope including all flow reactors of the present invention including the flow reactor of FIG. 1. In the explanation of the example of FIG. 3, the same constituents as those in FIG. 2 are given the same reference numerals, and are not described in detail.

In the manufacturing facility 200 of FIG. 3, raw material feeding lines 14$g$ and 14$h$ are connected to raw material tanks 31$g$ and 31$h$, respectively, and raw materials (K, L) sent out from the respective tanks are fed to the lines 14$g$ and 14$h$ by pumps 21$g$ and 21$h$, respectively. The reaction product (M) is sent to a receiver tank 32 coupled to a discharge line 15$g$. Depending on the type of reaction, a liquid 33 for quenching a reaction liquid may be placed in the receiver tank 32. By placing the liquid 33 in the receiver tank 32, safety can be further enhanced.

The manufacturing facility of FIG. 3 includes a circulation line 36 for a fluid 30, and a heat exchanger 37 is installed on the circulation line 36. Therefore, the temperature of the fluid 30 can be controlled, and the reaction temperature in the reactor unit 11$g$ can be controlled through the fluid 30.

The manufacturing facility of FIG. 3 further includes a stirrer (an impeller in the illustrated example) 34 in the vessel 22$q$. Therefore, the uniformity of the characteristics of the fluid 30 can be improved, and it is possible to improve the accuracy or efficiency for detecting leakage through the fluid, for rendering a leaked substance harmless by the fluid, or for heating or cooling the reactor by the fluid. In particular, in the example of FIG. 3, it is assumed that the pH of the fluid (water in the illustrated example) 30 becomes higher or lower when leakage occurs. By monitoring a value displayed on a pH meter 35 inserted into the vessel 22$q$, the presence or absence of leakage can be detected.

As the stirrer, a known means such as a fluid jet means can be employed in addition to the impeller as required.

When leakage is detected through a change in the characteristics of the fluid, the change in the characteristics includes not only a pH change but also a color change and a light scattering change as described above. When leakage is detected through a color change, a light scattering change, or the like, an appropriate observation means (sensor) such as a chromaticity meter, a scattered light measurement device, and a turbidimeter may be attached to a window through which the characteristics of the fluid in the vessel 22$q$ can be observed.

The position at which a sensor, such as a pH meter or a chromaticity meter, that reads the characteristics of the fluid is attached is not particularly limited as long as the characteristics of the fluid can be observed. For example, the sensor may be attached at any place in the vessel 22$q$ where the characteristics of the fluid can be observed, or at any place where the characteristics of the fluid 30 taken out from the vessel 22$q$ by an appropriate means such as a fluid outlet valve, a circulation means, and a sampling port can be observed.

When leakage is detected, a signal may be transmitted to an alarm generator, the raw material feeding pumps 21$g$ and 21$h$, or raw material feeding control valves 38$g$ and 38$h$ installed on the raw material feeding lines, whereby an alarm can be raised, or the feeding of the raw materials can be stopped.

(4) Method for Using

In each of the flow reactors 100 and 101, two or more attachable and detachable parts can be appropriately selected, and a section between the selected attachable and detachable parts can be removed and replaced with another configuration (hereinafter, sometimes referred to as a new configuration). Here, the new configuration refers to a configuration including one or more selected from line structure components including a raw material feeding line, a mixing unit, a reactor unit, and a discharge line. As long as the new configuration after replacement combined with the sections that have not been replaced can constitute a flow reactor (that is, can form one or more line structures as a whole), the new configuration to be attached may be part of the line structure (for example, a feeding line only, a mixing unit only, a reactor unit only, a discharge line only, or an appropriate combination thereof), or may be a combination of one or more line structures and part of another line structure (for example, a configuration formed of one line structure composed of a feeding line, a mixing unit, a reactor unit, and a discharge line, and a reactor unit connected to such a line structure). Furthermore, the new configuration may be the same as or different from the configuration of the section before replacement. When the configurations before and after replacement are the same, the flow reactor can be refreshed without changing the reaction mode. When the configurations before and after replacement are different, the reaction mode can be changed as appropriate.

Figure 4:
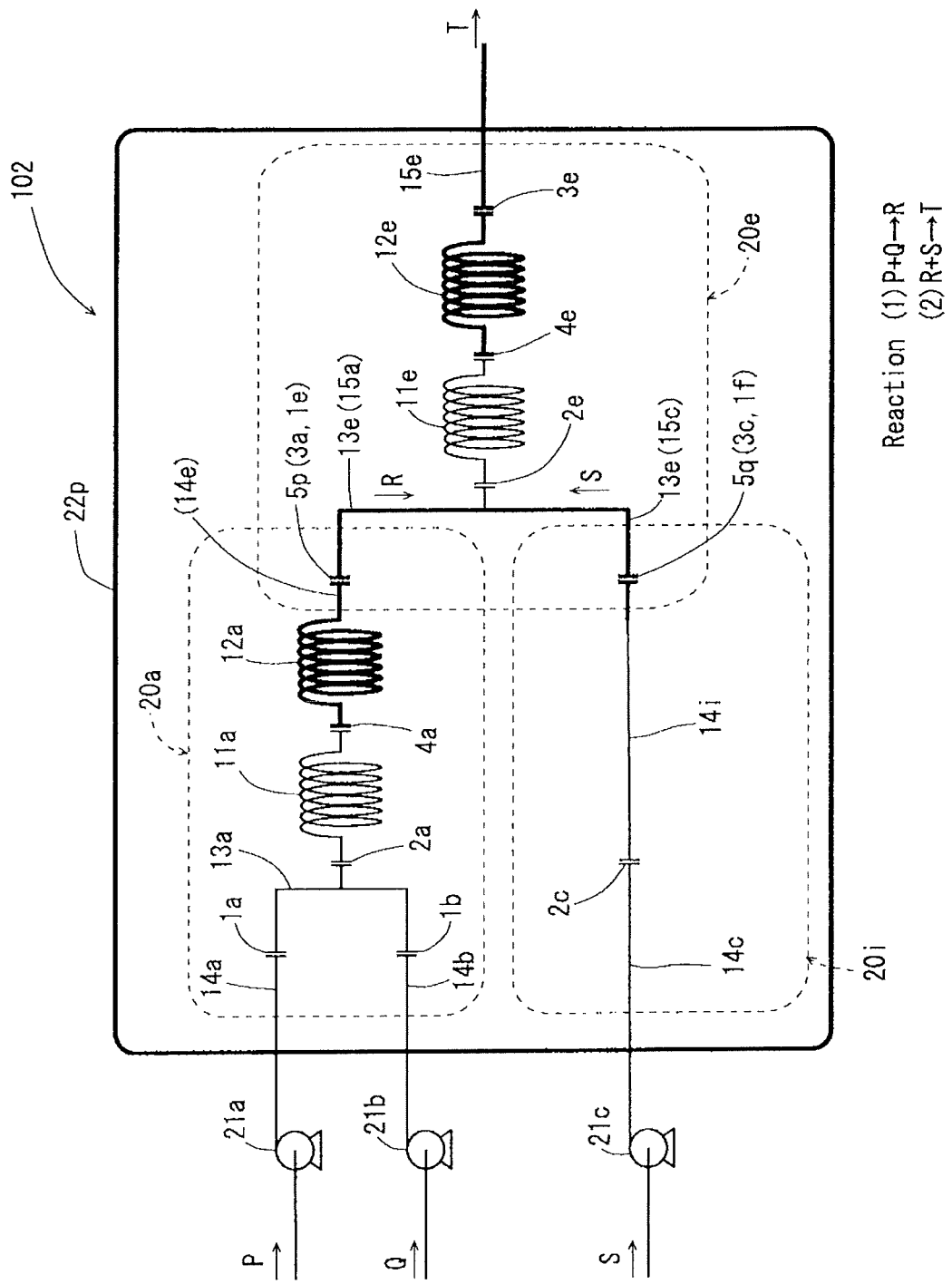
FIG. 4 is a schematic view of a flow reactor for explaining one example of a method for using a manufacturing facility of the present invention.
Figure 5:
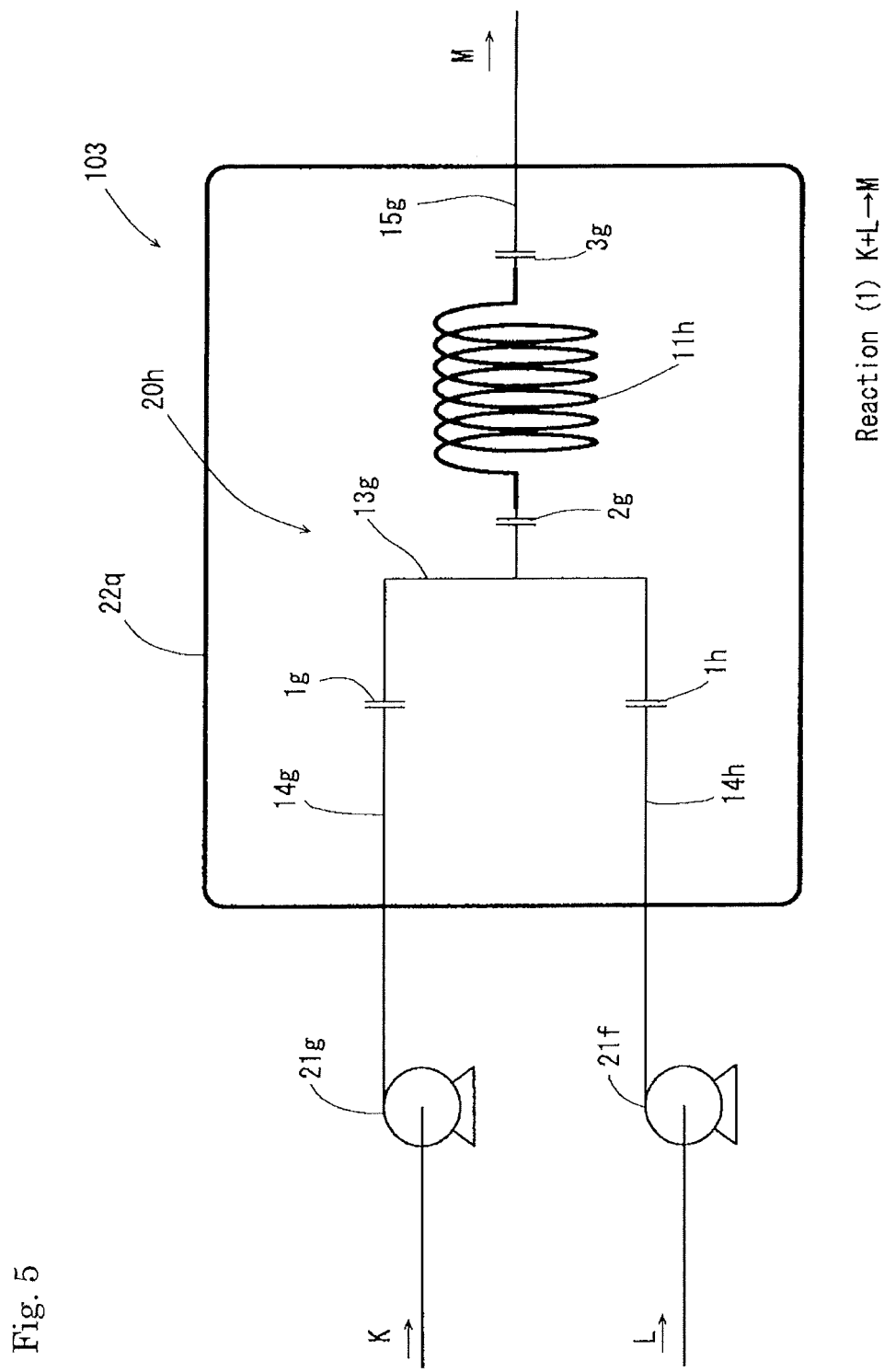
FIG. 5 is a schematic view of a flow reactor for explaining another example of a method for using a manufacturing facility of the present invention.

There are many examples in which the configurations before and after replacement are different, and some of these examples are illustrated. In the flow reactor 100 of FIG. 1, the line is disconnected at the connections 2$c$ and 5$q$ before and after the reactor unit to remove the reactor units 11$c$ and 12$c$, and a new raw material feeding line 14$i$ is installed to form another flow reactor 102 in which the line structure 20$c$ is changed to a line structure 20$i$ as shown in FIG. 4. In the flow type reactor 101 of FIG. 2, the line is disconnected at the connections 2$g$ and 3$g$ before and after the reactor unit to remove the reactor unit 11$g$, and a new reactor unit 11$h$ with an inner diameter different from the inner diameter of the former reactor unit 11$g$ is installed to form another flow reactor 103 as shown in FIG. 5.

The timing for replacement with the new configuration can be set as appropriate. For example, replacement with the new configuration may be performed at the timing of changing a raw material. More specifically, it is preferred to stop a flow stream from the raw material to the reaction product and start the flow stream after replacing with the new configuration and changing the raw material. The timing of changing the raw material includes the timing of switching a production item, the timing of changing a raw material lot, and the timing of switching from one small unit to another small unit when a raw material lot is divided into small units.

The timing of replacement with the new configuration may be at the time of the outage of the manufacturing facility (such as the time of shutdown of a plant), at the time of routine check of the manufacturing facility, at the time of parts replacement of the manufacturing facility, or the like.

(5) Reaction

A reaction using the above flow reactor is not particularly limited. A raw material to be fed may be a gas or a liquid, and a liquid raw material is often used. When a liquid raw material is used, for example, the flow reactor is preferably used to react a solution containing a compound having an SH group, an OH group, an $NH_2$ group, or an NHR group (where R represents an organic group) with a solution containing an activated carbonyl compound such as phosgene or triphosgene. The SH group, the OH group, or the NHR group reacts with phosgene or triphosgene, and a compound in which ClC(=O)-group is bonded instead of a hydrogen atom in the SH group, the OH group, or the NHR group is formed. The $NH_2$ group reacts with phosgene or triphosgene to be isocyanated. When a compound having two or more of the SH group, the OH group, the NHR group, and the like is used as a raw material to allow to react with phosgene, triphosgene, or the like, a compound can be formed in which a hydrogen atom is removed from each of two groups selected from the SH group, the OH group, the NHR group, and the like, and the groups are linked via a carbonyl group. In such a reaction, even if the raw material liquid or the reaction liquid containing phosgene, triphosgene, or the like leaks from the connections, the leaked substance can be kept in the vessel by using the flow reactor of the present invention, so that safety can be maintained. In addition, if water or an aqueous solution is used as a fluid to be accommodated in the vessel, phosgene, triphosgene, and the reaction liquid leaking from the connections can be quenched, so that safety can be maintained. Furthermore, by observing the pH of water or the aqueous solution, the leakage of the raw material liquid or the reaction liquid can also be detected.

When triphosgene is used, it is preferred to also use an amine as a raw material. The use of an amine allows triphosgene to quickly change to phosgene, and the reaction with a compound having an SH group, an OH group, an $NH_2$ group, or an NHR group (where R represents an organic group) can be accelerated.

When a compound having an SH group, an OH group, an $NH_2$ group, or an NHR group (wherein R represents an organic group), triphosgene, and an amine are used as raw materials, the three raw materials may be fed from separate raw material feeding lines, mixed in a single mixing unit, and then reacted in the reactor unit; or a mixture obtained by mixing the two raw materials in advance may be fed from a raw material feeding line, the remaining raw material may be fed from another raw material feeding line, and both may be mixed in the mixing unit and then reacted in the reactor unit.

The present application claims priority based on Japanese Patent Application No. 2017-148083 filed on Jul. 31, 2017.

All the contents described in Japanese Patent Application No. 2017-148083 filed on Jul. 31, 2017 are incorporated herein by reference.

DESCRIPTION OF REFERENCE NUMERALS

200: manufacturing facility
100, 101, 102, 103: flow reactor
22*p*, 22*q*: vessel
20*a*, 20*c*, 20*e*, 20*g*, 20*i*: line structure
14*a*, 14*b*, 14*c*, 14*e*, 14*f*, 14*g*, 14*h*, 14*i*: raw material feeding line
13*a*, 13*e*, 13*g*: mixing unit
11*a*, 12*a*, 11*c*, 12*c*, 11*e*, 12*e*, 11*g*: reactor unit
15*a*, 15*c*, 15*e*, 15*g*: discharge line
1*a*, 1*b*, 1*e*, 1*f*, 1*g*, 1*h*, 2*a*, 2*c*, 2*e*, 2*g*, 3*a*, 3*c*, 3*e*, 3*g*, 4*a*, 4*c*, 4*e*, 5*p*, 5*q*: joint portion (attachable and detachable connection)
30: fluid.

The invention claimed is:

1. A flow reactor, comprising:
at least one line structure each comprising a raw material feeding line, a reactor unit configured to react a raw material fed from the raw material feeding line therein, and a discharge line configured to discharge a reaction product produced in the reactor unit; and
a vessel accommodating a part or all of the reactor unit and a fluid such that the part or all of the reactor unit and the fluid are capable of contacting with each other,
wherein each of the at least one line structure comprises two or more attachable and detachable connections,
wherein at least one of the two or more attachable and detachable connections is accommodated in the vessel, and
wherein the fluid comprises at least one selected from the group consisting of water, an aqueous solution, an alcohol, and ether.

2. The flow reactor according to claim 1, wherein the at least one line structure comprises a line structure having two or more raw material feeding lines, and, between the two or more raw material feeding lines and the reactor unit, a mixing unit configured to mix raw materials fed from the two or more raw material feeding lines and send a mixture to the reactor unit.

3. The flow reactor according to claim 1, wherein the attachable and detachable connections are arranged on an upstream side of the reactor unit and a downstream side of the reactor unit in each of the at least one line structure.

4. The flow reactor according to claim 2, wherein the attachable and detachable connections are arranged on an upstream side of the mixing unit and a downstream side of the reactor unit in each of the at least one line structure.

5. The flow reactor according to claim 1, wherein at least two of the two or more attachable and detachable connections are accommodated in the vessel.

6. The flow reactor according to claim 1, wherein the fluid is a liquid and is capable of quenching a leaked substance leaked from the at least one line structure, has a characteristic changeable when contacting the leaked substance, is heat-exchangeable with at least a part of the at least one line structure, or is capable of supporting the reactor unit.

7. The flow reactor according to claim 6, wherein the vessel comprises a gas portion which is a space not filled with a liquid such that at least a part of the reactor unit is exposed to the gas portion without contacting the liquid.

8. The flow reactor according to claim 1, wherein the vessel is a closed vessel capable of isolating contents of the vessel from outside.

9. The flow reactor according to claim 1, wherein the reactor unit comprises a flow channel having an inner diameter of from 0.1 mm to 50 mm.

10. The flow reactor according to claim 1, wherein the reactor unit has a shape comprising at least one bent part.

11. A manufacturing facility, comprising:
the flow reactor according to claim 1.

12. The manufacturing facility according to claim 11, wherein the fluid accommodated in the vessel of the flow reactor is a medium which characteristic is changeable when contacting a reaction liquid, and the manufacturing facility further comprises a sensor capable of detecting the change of the characteristic.

13. A method for using the manufacturing facility according to claim 11, the method comprising, when a raw material is fed to the manufacturing facility to obtain a reaction product:
selecting at least two attachable and detachable connections from the two or more attachable and detachable connections and removing a section between the selected attachable and detachable connections; and
replacing the removed section with a new configuration comprising one or more line structure components selected from the group consisting of a raw material feeding line, a mixing unit, a reactor unit, and a discharge line.

14. The method according to claim 13, further comprising:
stopping a flow stream in the manufacturing facility to stop production of the reaction product from the raw material;
replacing the section between the selected attachable and detachable connections and changing the raw material; and
after the replacing and the changing, starting the flow stream.

15. The method according to claim 13, further comprising:
stopping a flow stream in the manufacturing facility to stop production of the reaction product from the raw material;
replacing the section between the selected attachable and detachable connections and temporarily stopping operation of the manufacturing facility, conducting a routine check, and/or replacing one or more parts of the manufacturing facility; and then
starting the flow stream.

16. The flow reactor according to claim 1, wherein the fluid comprises an inert gas or a non-reactive solution that does not react with the raw material or the reaction product.

* * * * *